US 6,660,473 B1

(12) United States Patent
Lohse et al.

(10) Patent No.: US 6,660,473 B1
(45) Date of Patent: Dec. 9, 2003

(54) C-TERMINAL PROTEIN TAGGING

(75) Inventors: Peter Lohse, Weston, MA (US); Michael McPherson, Johnston, RI (US); Robert G. Kuimelis, Brighton, MA (US)

(73) Assignee: Phylos, Inc., Lexington, MA (US)

( * ) Notice: Subject to any disclaimer, the term of this patent is extended or adjusted under 35 U.S.C. 154(b) by 107 days.

(21) Appl. No.: 09/614,264

(22) Filed: Jul. 12, 2000

Related U.S. Application Data

(60) Provisional application No. 60/143,339, filed on Jul. 12, 1999.

(51) Int. Cl.$^7$ .................. C12Q 1/688; C12P 19/34; G01N 33/00; A61K 38/00; C07K 1/00
(52) U.S. Cl. .................. 435/6; 435/91.1; 436/94; 530/300; 530/350
(58) Field of Search .................. 435/6, 91.1, 91.2, 435/91.21, 91.51, 183, 69.1, 69.7, 71.1; 436/94; 536/23.1, 25.3, 25.41; 530/300, 333, 344, 350

(56) References Cited

U.S. PATENT DOCUMENTS 5,723,584 A * 3/1998 Schatz
6,228,994 B1 * 5/2001 Yanagawa et al.

FOREIGN PATENT DOCUMENTS

| JP | 98-320093 | 5/2000 |
| WO | WO 98/31700 | 7/1998 |
| WO | WO 99/51773 | 10/1999 |
| WO | WO 00/09737 | 2/2000 |
| WO | WO 00/32823 | 6/2000 |

OTHER PUBLICATIONS

Eggers et al., Complexes between nascent polypeptides and their molecular chaperones in the cytosol of mammalian cells. Mol. Bio. Cell, 8, 1559–1573, Aug. 1997.*

Drijfhout et al., "Solid–Phase Synthesis and Applications of N–(S–Acetylmercaptoacetyl) Peptides," *Anal. Biochem.* 187:349–354 (1990).

Hanes & Pluckthun, "In vitro Selection and Evolution of Functional Proteins by Using Ribosome Display," *Proc. Natl. Acad. Sci. USA* 94:4937–4942 (1997).

McPherson et al., C–Terminal Protein Tagging, 5$^{th}$ Annual Conference and Exhibition (Sep. 13–16, 1999).

Pestka, "Peptidyl–Puromycin Synthesis on Polyribosomes from Rat Liver or Brain," *Meth. Enzymol.* 30:479–488 (1974).

Roberts and Szostak, "RNA–Peptide Fusions for the in vitro Selection of Peptides and Proteins," *Proc. Natl. Acad. Sci. USA* 94:12297–12302 (1997).

Rose et al., "Attachment of Linker Groups to Carboxyl Termini Using Enzyme–Assisted Reverse Proteolysis," *Peptides* 1988 (G. Jung and E. Bayer, eds.) pp. 274–276, Walter de Gruyter & Co., New York (1989).

Schwarz et al. "Enzymatic C–Terminal Biotinylation of Proteins," *Meth. Enzymol.* 184:160–162 (1990).

Vince et al. "Carbocyclic Puromycin: Synthesis and Inhibition of Protein Biosynthesis," *J. Med. Chem.* 29:2400–2403 (1986).

Wetzel et al., "A General Method for Highly Selective Cross–Linking of Unprotected Polypeptides via pH–Controlled Modification of N–Terminal α–Amino Groups," *Bioconjugate Chem.* 1:114–122 (1990).

* cited by examiner

*Primary Examiner*—Ethan Whisenant
*Assistant Examiner*—Frank Lu
(74) *Attorney, Agent, or Firm*—Clark & Elbing LLP

(57) ABSTRACT

In general, the invention features proteins having covalently bonded C-terminal puromycin tags and methods for their production.

18 Claims, 11 Drawing Sheets

C-TERMINAL PROTEIN TAGGING

CROSS REFERENCE TO RELATED APPLICATIONS

This application claims the benefit of the filing date of provisional application, U.S. Ser. No. 60/143,339, filed Jul. 12, 1999, now abandoned.

BACKGROUND OF THE INVENTION

In general, the invention relates to methods of labeling proteins.

Covalent conjugates of polypeptides with non-peptide "labels" or "tags" form a useful class of reagents in protein research. A conjugate is usually intended to retain the native properties of the protein while gaining a new, non-native property due to the label. Biotinylation, for example, permits proteins to be separated, quantified, or immobilized by mechanisms based on the strong interaction of biotin with avidin or streptavidin (Bayer & Wilchek (1990) Protein Biotinylation, Meth. Enzymol. 184:138–160). Fluorescent or metal-chelating groups can also be introduced to generate newly modified proteins.

It would be convenient to be able to introduce a non-protein label as the protein is produced, but this is only sometimes feasible, for example, if the peptide can be produced by chemical synthesis, and is impractical when the protein is produced biologically. Generally, the conjugate must be formed by treating the peptide with a functional group-specific reagent that contains the label. Moreover, unless the peptide contains only one group attacked by the reagent, this procedure generally yields a mixture of products. This random form of labeling is sometimes adequate, but it is often preferable to modify a protein at a single specified site and to employ the modified product in purified form. For such cases, it would be valuable to have a method of directing the modifying group to a single, preselected location. Such a precisely targeted modification is termed site-directed protein tagging.

SUMMARY OF THE INVENTION

In general, the invention features a protein having a covalently bonded puromycin-tag, the tag being positioned at the C-terminal end of the protein.

In preferred embodiments, the tag is a small molecule (for example, biotin); the tag is a detectable label (for example, fluorescein, rhodamine, or BODIPY, or derivatives thereof); the tag is a functional group (for example, a functional group having a reactivity orthogonal to the reactivity of one of the protein's functional groups); the tag is a tether for attachment to a solid support (for example, a column, bead, or chip); the tag is one member of a specific binding pair; the tag is a phenyl diboronic acid derivative; the puromycin-tag further includes a nucleotide sequence positioned between the tag and the puromycin; and the nucleotide sequence is between about 1–200 nucleotides in length.

In a related aspect, the invention features a method for C-terminal protein tagging, involving (a) providing a nucleic acid sequence encoding the protein; (b) translating the sequence under conditions in which translation stalls at the 3' end of the sequence, forming a stalled translation complex; and (c) contacting the stalled translation complex with a puromycin-tag under conditions in which the puromycin-tag is covalently bonded to the C-terminus of the protein.

In preferred embodiments, the tag is attached to the 5'-hydroxy group of puromycin; the tag is attached to the 5'-hydroxy group of the puromycin through a phosphate group; the nucleic acid sequence encoding the protein contains no stop codons; the translation step is carried out in the substantial absence of at least one translation release factor; the 3'-end of the nucleic acid sequence encoding the protein is covalently linked to a DNA oligomer; the tag is a small molecule (for example, biotin); the tag is a detectable label (for example, fluorescein, rhodamine, or BODIPY, or a derivative thereof); the tag is a functional group; the protein has a first functional group and the tag is a second functional group, wherein the first functional group has a reactivity orthogonal to the reactivity of the second functional group; the tag is a tether for attachment to a solid support (for example, a column, bead, or chip); the tag is one member of a specific binding pair; the tag is a phenyl diboronic acid derivative; the puromycin-tag further includes a nucleotide sequence positioned between the tag and the puromycin; and the nucleotide sequence is between about 1–200 nucleotides in length.

By a "protein" is meant any two or more naturally occurring or modified amino acids joined by one or more peptide bonds. "Protein," "peptide," and "polypeptide" are used interchangeably herein.

By a "puromycin-tag" is meant puromycin having a covalently bonded structural or functional moiety which is not native to the puromycin molecule and which is chosen from the group consisting of a detectable label, a chemically reactive functional group, a small molecule, a protein or peptide, a peptoid, a naturally occurring or non-naturally occurring polymer, a solid-phase bound tether, a carbohydrate, or a nucleic acid (preferably, of between about 1–200 nucleotides) which does not encode the protein to which the puromycin-tag is itself covalently linked. By a "nucleic acid" is meant any two or more covalently bonded, naturally occurring or modified nucleotides and includes DNA, RNA, and PNA. Preferred puromycin-nucleic acid tags include 5'-C-C-puromycin-3'.

By a "small molecule" is meant a molecule having a molecular weight of approximately 2000 Daltons or less, preferably, 1500 Daltons or less, more preferably, 1000 Daltons or less, and, most preferably, 500 Daltons or less.

By a "functional group" is meant any moiety of, or arrangement of atoms in, a molecule which exhibit some chemical reactivity.

The present invention provides a number of advantages over current chemical and enzymatic protein-tagging methods. For example, the tag is introduced in the final step of translation on the ribosome. This modification is advantageous because tagged proteins may be generated in a single preparative step. In addition, the tag is introduced in translation buffer under conditions which enhance protein stability. Again, this provides for increased product yield and optimized protein quality. In particular, although several schemes for N-terminal (Drijfhout et al. (1990) Anal. Biochem. 187: 349–354; Wetzel et al. (1990) Bioconjugate Chem. 1: 114–122) and C-terminal (Schwarz et al. (1990) Meth. Enzymol. 184: 160–162; Rose et al. (1989) Peptides 1988 (G. Jung and E. Bayer, eds.) pp. 274–276, Walter de Gruyter & Co., New York) tagging have been described, many of these methods involve a tagging step that is carried out under conditions which disrupt protein structure. For example, modification at non-physiological pH and temperature or in the presence of non-aqueous solvents or chemicals, followed by purification of the modified protein, disrupts folding thus leading to a non-functional product. In contrast, the present tagging method is performed under native conditions. Finally, in yet another advantage, the present invention enables the introduction of a tag regioselectively at the C-terminus of a protein, facilitating the production of native proteins carrying desired C-terminal structural or functional elements in a simple and efficient way.

The C-terminally tagged polypeptides and proteins produced by the methods of the present invention may be used in any appropriate technique, for example, in any affinity purification method, protein detection method (for example, using proteins having C-terminal fluorescein tags), structure function or protein dynamics analyses (for example, using proteins having C-terminal reporter tags), pharmaceutical analyses (for example, using proteins having detectable C-terminal tags which allow for a determination of cellular protein uptake or cellular localization), or protein display technology (for example, using solid phase tags to generate protein arrays on microchips).

Other features and advantages will be apparent from the following detailed description and from the claims.

DETAILED DESCRIPTION

The present invention makes use of puromycin, an antibiotic that mimics the aminoacyl end of tRNA, as a vehicle to introduce a tag at the C-terminus of a protein. The puromycin acts as a translation inhibitor by entering the ribosomal A site and accepting the nascent protein as a result of the peptidyl transferase activity of the ribosome (Monro & Marcker (1967) J. Mol. Biol. 25: 347–350; Monro & Vazquez (1967) J. Mol. Biol. 28: 161–165). The resulting peptidyl-puromycin molecule contains a stable amide linkage between the peptide and the O-methyl tyrosine portion of the puromycin.

Figure 1:
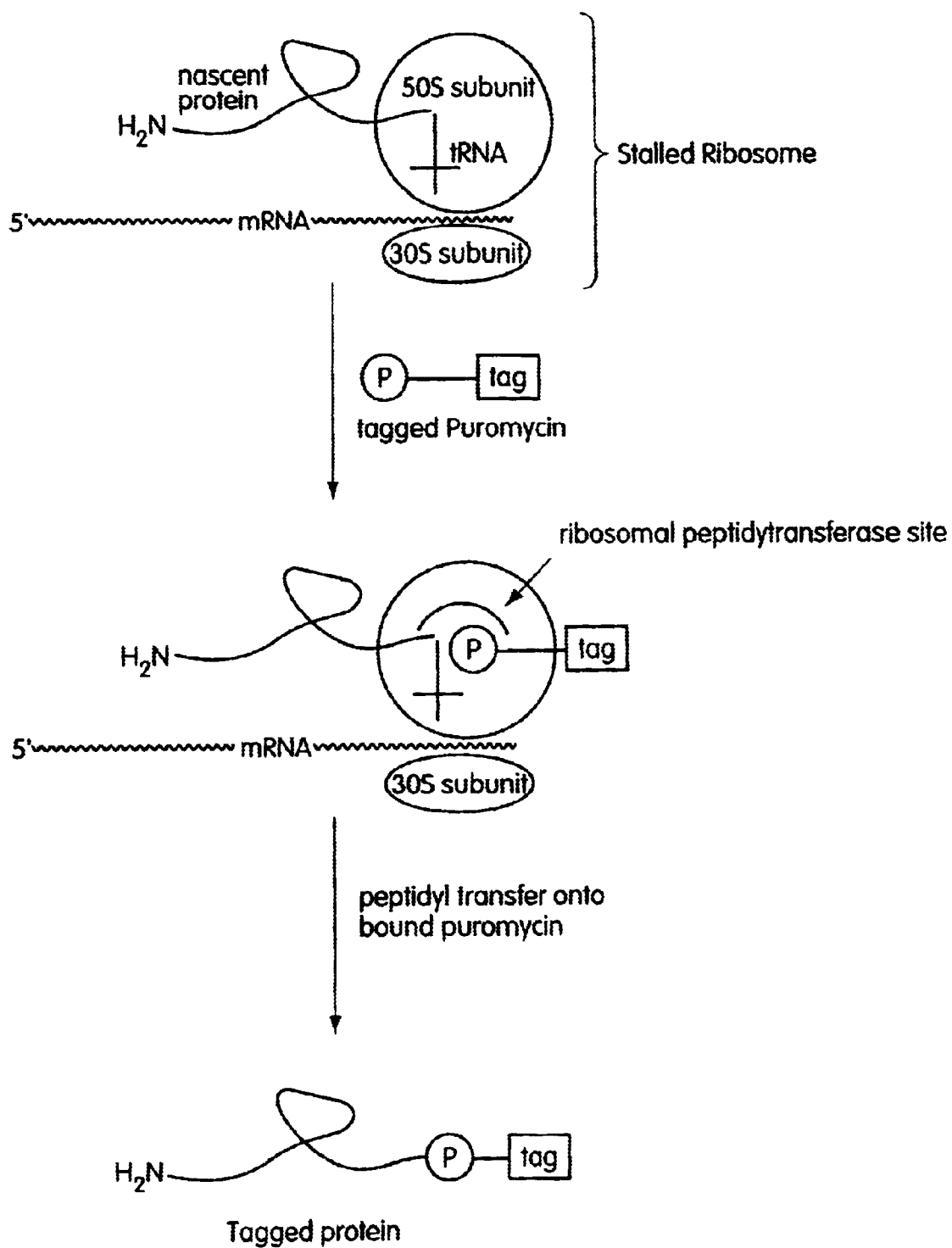
FIG. 1 is a schematic illustration of the preparation of a C-terminally tagged protein according to the present invention.

A desired tag is linked to the puromycin moiety in such a way that binding as well as peptidyl acceptor functionality of the puromycin is only slightly decreased or is not decreased at all. Following translation, binding of the tagged puromycin by the ribosome followed by peptidyl transfer onto the primary amino group of puromycin yields the desired C-terminally tagged protein. This technique is shown schematically in FIG. 1.

Different positions of puromycin can serve as anchor points for attachment of tags, although puromycin functional groups not involved in ribosome binding represent preferred anchor points for attachment. In one particular example, it has been shown that the 5'-hydroxymethyl group of puromycin does not contribute to ribosome binding (Vince et al. (1981) J. Med. Chem. 24: 1511). In addition, nucleic acids carrying a 3'-terminal puromycin have been shown to bind to the ribosome. Accordingly, the 5'-hydroxy group of puromycin is a preferred position for attachment of a desired tag (Szostak et al., WO 98/31700; Roberts & Szostak (1997) Proc. Natl. Acad. Sci. USA 94: 12297–12302).

The attachment of additional nucleotides (preferably, between about 1–200 nucleotides) at the 5'-hydroxymethyl group of puromycin may, in some cases, further enhance the ability of puromycin to enter the ribosomal A site and to act as an effective tRNA substitute. No particular sequence of nucleotides is required for this purpose. In this case, the desired tag is linked through the 5'-position of whatever terminal nucleotide is employed. Such derivatives are referred to herein as $X_n$-puromycin derivatives.

The tag can be any non-native structural or functional element. Small molecules, natural products, non-natural polymers, and solid-phase bound tethers represent tags according to the invention. Examples of preferred small molecules include, without limitation, biotin and fluorescein or any other detectable label. Examples of natural products include, without limitation, peptides, proteins, nucleic acids, and carbohydrates. Peptoids are an example of a preferred non-natural polymer tag (Zuckermann et al., J. Am. Chem. Soc. (1992) 114: 10646). Alternatively, the tag may be any functional group. Examples of useful functional groups include those with reactivities orthogonal to the reactivities of protein functional groups, for example, double bonds and ketones. In another aspect of the invention, the tag may be a tether linked to a solid phase. Such tags enable the ready attachment of peptides and proteins to columns, beads, or chip surfaces.

Any appropriate type of ligation chemistry may be exploited to attach the tag to the puromycin moiety and, for example, to the 5'-hydroxy group of the puromycin. In a preferred embodiment of the invention, the puromycin-tags are synthesized using standard solid phase techniques, for example, as outlined in FIG. 2. Commercially available phosphoramidites of biotin or fluorescein (Glen Research), for example, may be used to derivatize the 5'-terminus of puromycin or $X_n$-puromycin. These reactions may be carried out, for example, as described in Oligonucleotide Synthesis: A Practical Approach, ed. Gait, M. J. (IRL, Oxford).

Figure 2:
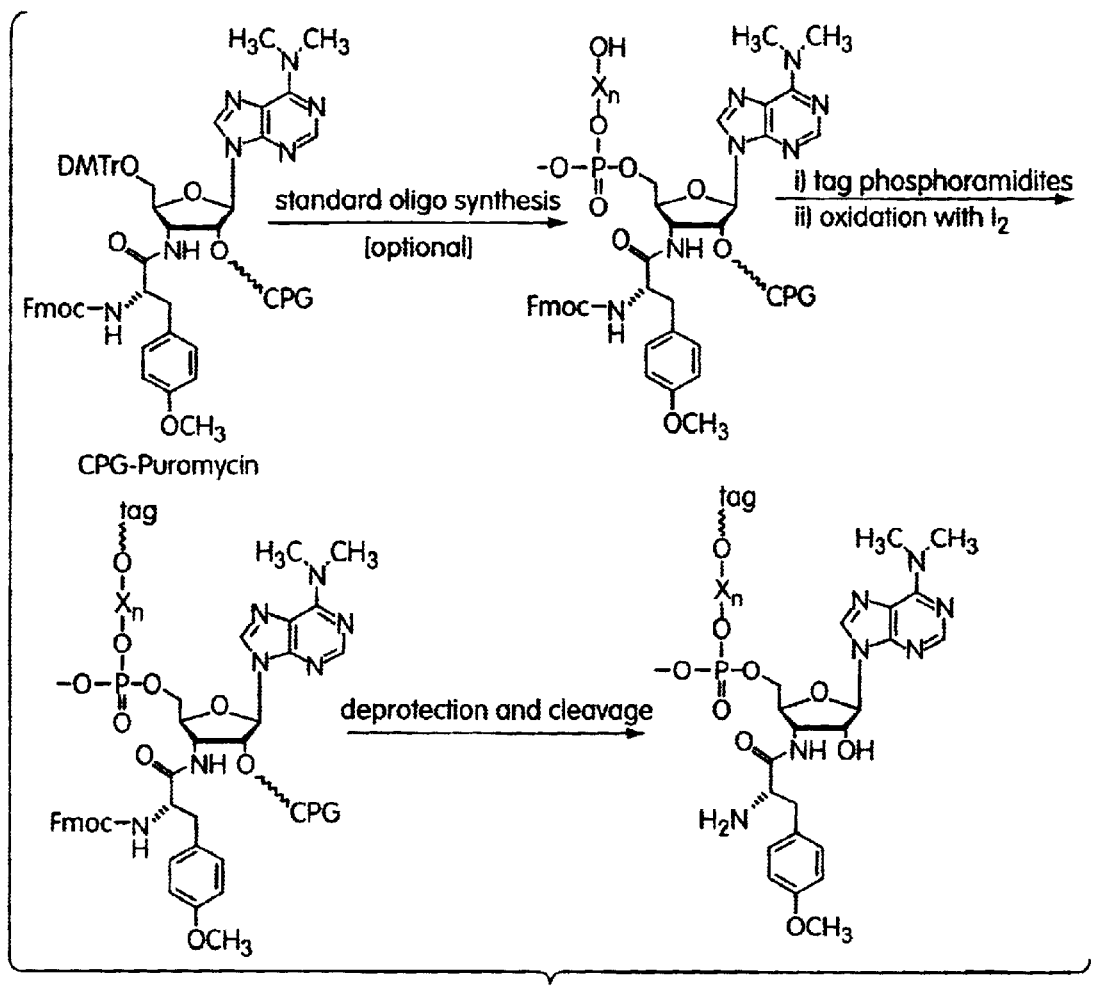
FIG. 2 is a schematic illustration of an exemplary method for the attachment of a tag to a puromycin or oligonucleotide-puromycin ($X_n$-puromycin) derivative through a 5'-phosphodiester linkage.

Using the synthetic scheme shown in FIG. 2, any number of 5'-tagged puromycin derivatives or $X_n$-puromycin derivatives may be readily produced.

Figure 4:
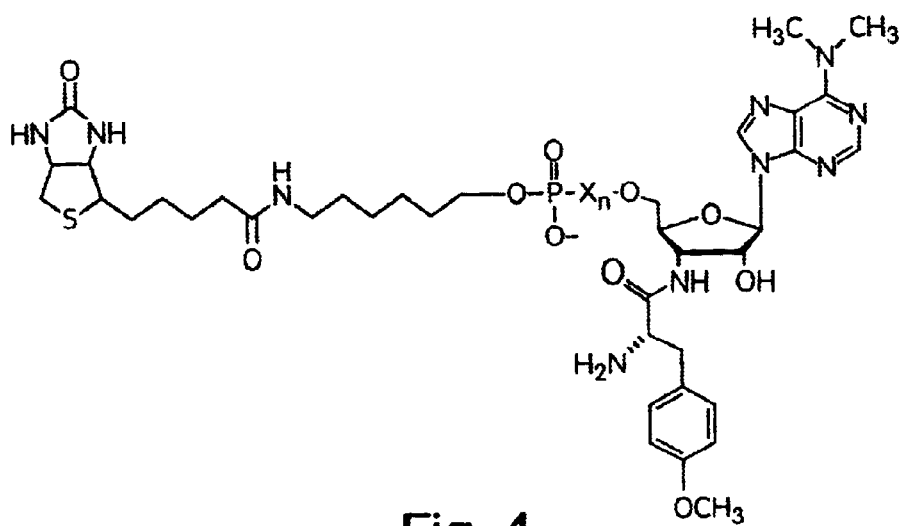
FIG. 4 is a schematic illustration of an $X_n$-puromycin-5'-phosphate carrying a 5'-tethered biotin.
Figure 5:
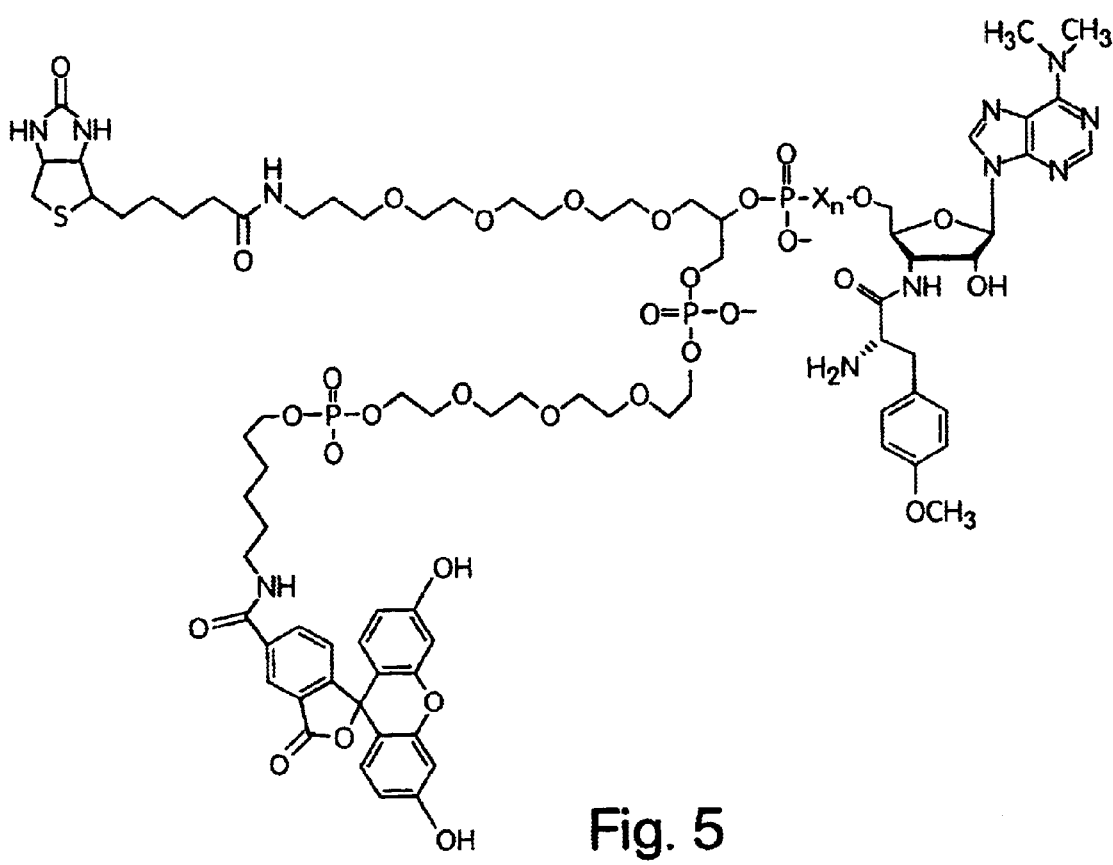
FIG. 5 is a schematic illustration of an $X_n$-puromycin 5'-phosphate carrying both biotin and fluorescein groups.

These derivatives include puromycin or $X_n$-puromycin linked to small molecules, for example, $X_n$-puromycin-5'-phosphate carrying a tethered biotin derivative (FIG. 4); such a puromycin or $X_n$-puromycin-tag may be used to attach a C-terminal biotin label to a protein, for example, for affinity purification. In a further example, a puromycin or $X_n$-puromycin-tag may act as a bifunctional reagent by using a puromycin or $X_n$-puromycin derivative which contains both attachment and detection groups, for example, as shown in FIG. 5. In this example, an $X_n$-puromycin derivative is tethered through its 5'-phosphate to both biotin and fluorescein moieties using standard oligonucleotide synthesis techniques. Attachment groups may include, without limitation, biotin, phenyl diboronic acid/salicylhydroxamic acid, 1,2-amino thiol, or ketone. Detection groups may include, without limitation, fluorescein or derivatives thereof, rhodamine or derivatives thereof, or BODIPY (4,4-difluoro-4-bora-3a,4a-diaza-s-indacene, Molecular Probes, Eugene, Oreg.) or derivatives thereof.

Figure 6:
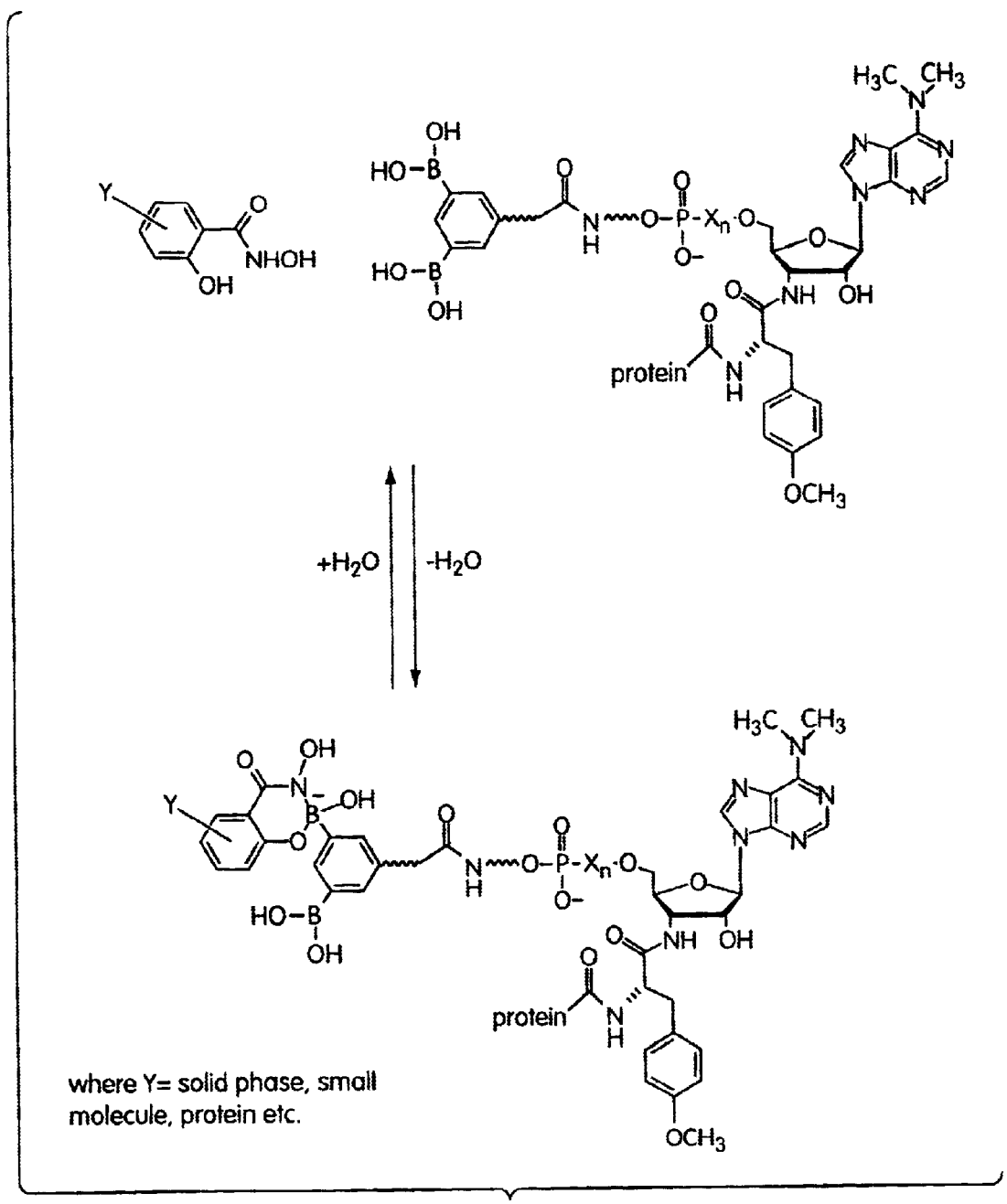
FIG. 6 is a schematic illustration of the reversible attachment of a protein-linked $X_n$-puromycin-5'-phosphate carrying a 5'-tethered phenyl diboronic acid to a salicylhydroxamic acid derivative.

In a further example, a puromycin or $X_n$-puromycin 5'-phosphate carrying a phenyl diboronic acid (PDBA) derivative may also be used to label the C-terminus of a peptide or protein for the purpose of purification or immobilization, as shown, for example, in FIG. 6. This reaction is carried out, for example, according to the manufacturer's instructions (Linx™ AP system, Invitrogen, Carlsbad, Calif.). In this example, the PDBA moiety interacts specifically with a salicylhydroxamic acid derivative to form a covalent complex (Linx™ AP system, Invitrogen, Carlsbad, Calif.). The interaction is reversible under certain pH conditions.

Figure 3:
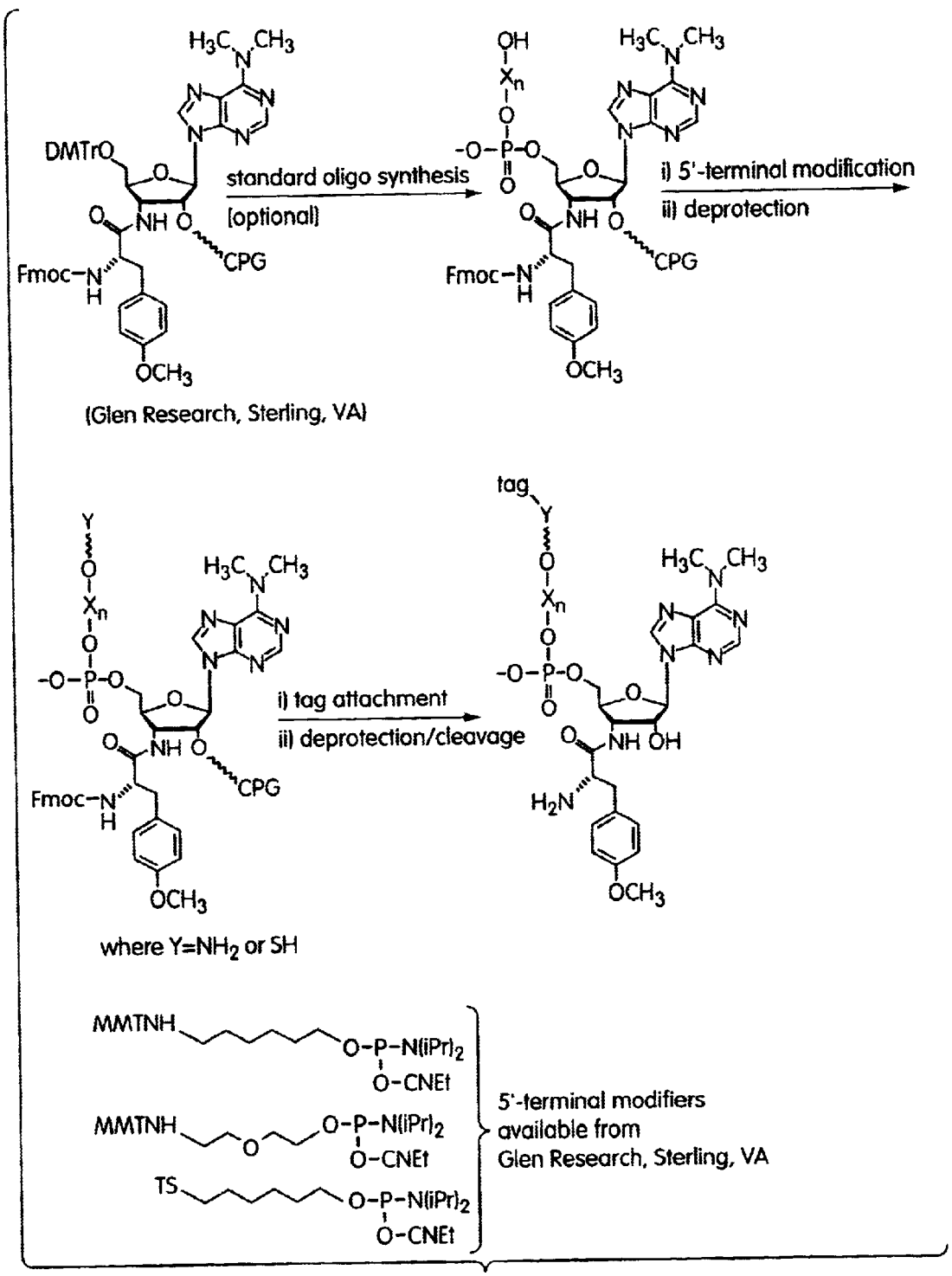
FIG. 3 is a schematic illustration of an exemplary method for the attachment of tags to puromycin or $X_n$-puromycin with 5'-terminal modified amino or thiol linkers.
Figure 7:
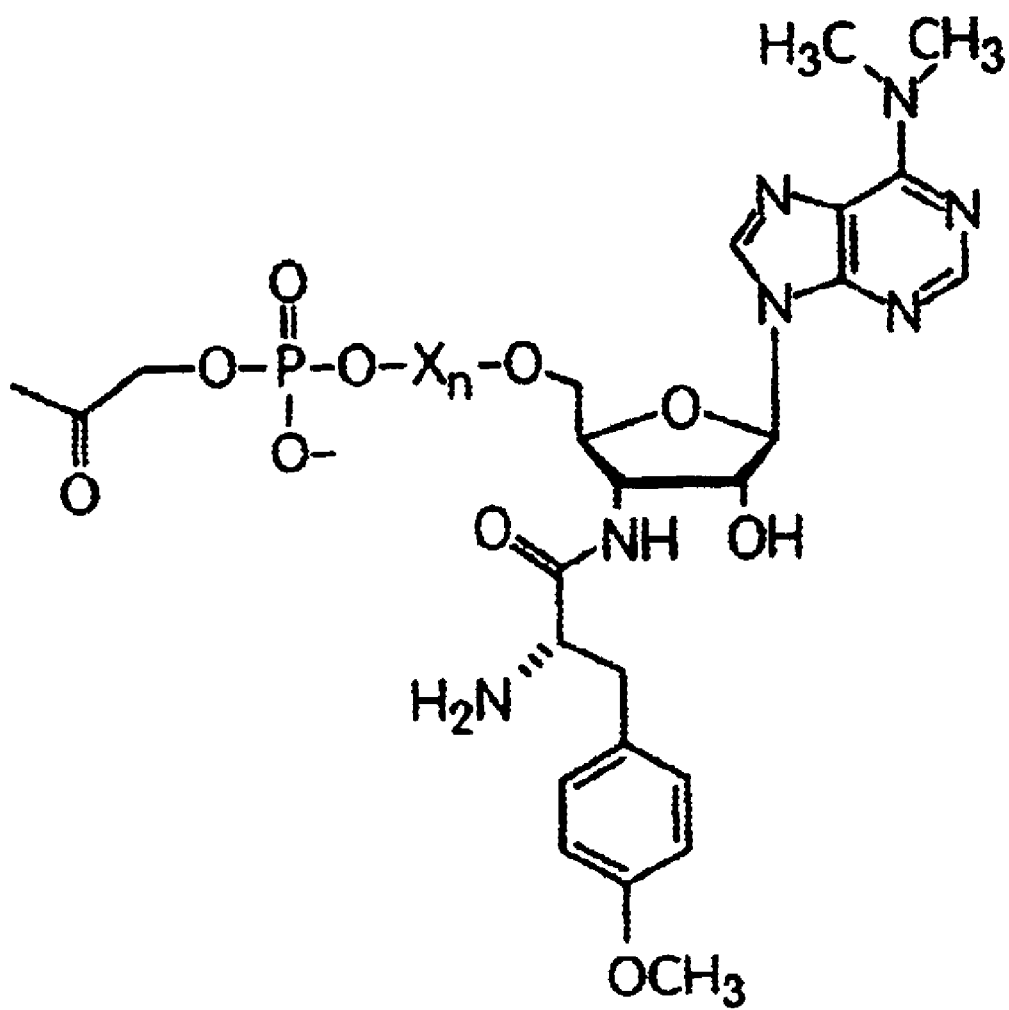
FIG. 7 is a schematic illustration of an $X_n$-puromycin-5'-phosphate carrying a 5'-ketone group.

The scheme in FIG. 3 outlines the synthesis of puromycin- or $X_n$-puromycin-tags which include a terminal modification that introduces a terminal amino or thiol functionality into the puromycin or $X_n$-puromycin intermediate. These reactions are again carried out as described above for FIG. 2. As illustrated in FIG. 7, these reactive moieties are then used to introduce non-protein functional groups, for example, a ketone, into the puromycin- or $X_n$-puromycin-tag.

Figure 8:
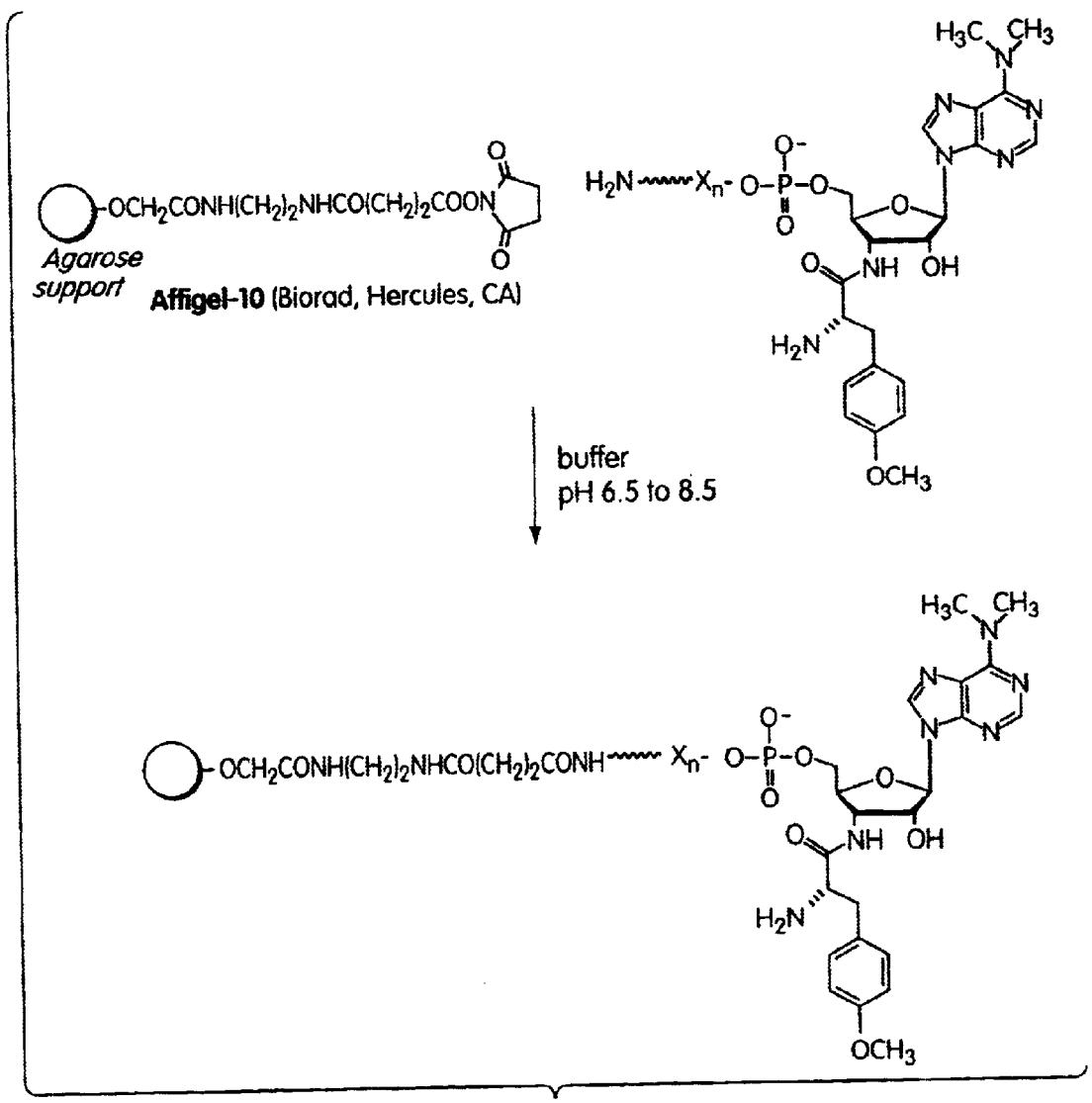
FIG. 8 is a schematic illustration of an exemplary method for the attachment of a 5'-terminal amino $X_n$-puromycin to an N-hydroxy succinimide activated agarose gel (AffiGel).

The synthetic scheme illustrated in FIG. 3 may also be used to link puromycin to a solid phase, as shown in FIG. 8. The solid phase may be any appropriate solid support including, without limitation, any column, plate, tube, bead, or chip. In the example illustrated in FIG. 8, a 5'-terminal amino functionalized puromycin or $X_n$-puromycin is used to derivatize an N-hydroxysuccinimide-activated agarose support (for example, Affi-Gel 10 or 15; Biorad, Hercules, Calif.) to generate an immobilized puromycin or $X_n$-puromycin derivative where, in this example, the solid support is the tag. This step is carried out according to the manufacturer's instructions (Affi-Gel; Biorad, Hercules, Calif.). The puromycin or $X_n$-puromycin tethered to the solid phase may then be utilized in the purification and/or immobilization of peptides or proteins.

Figure 9:
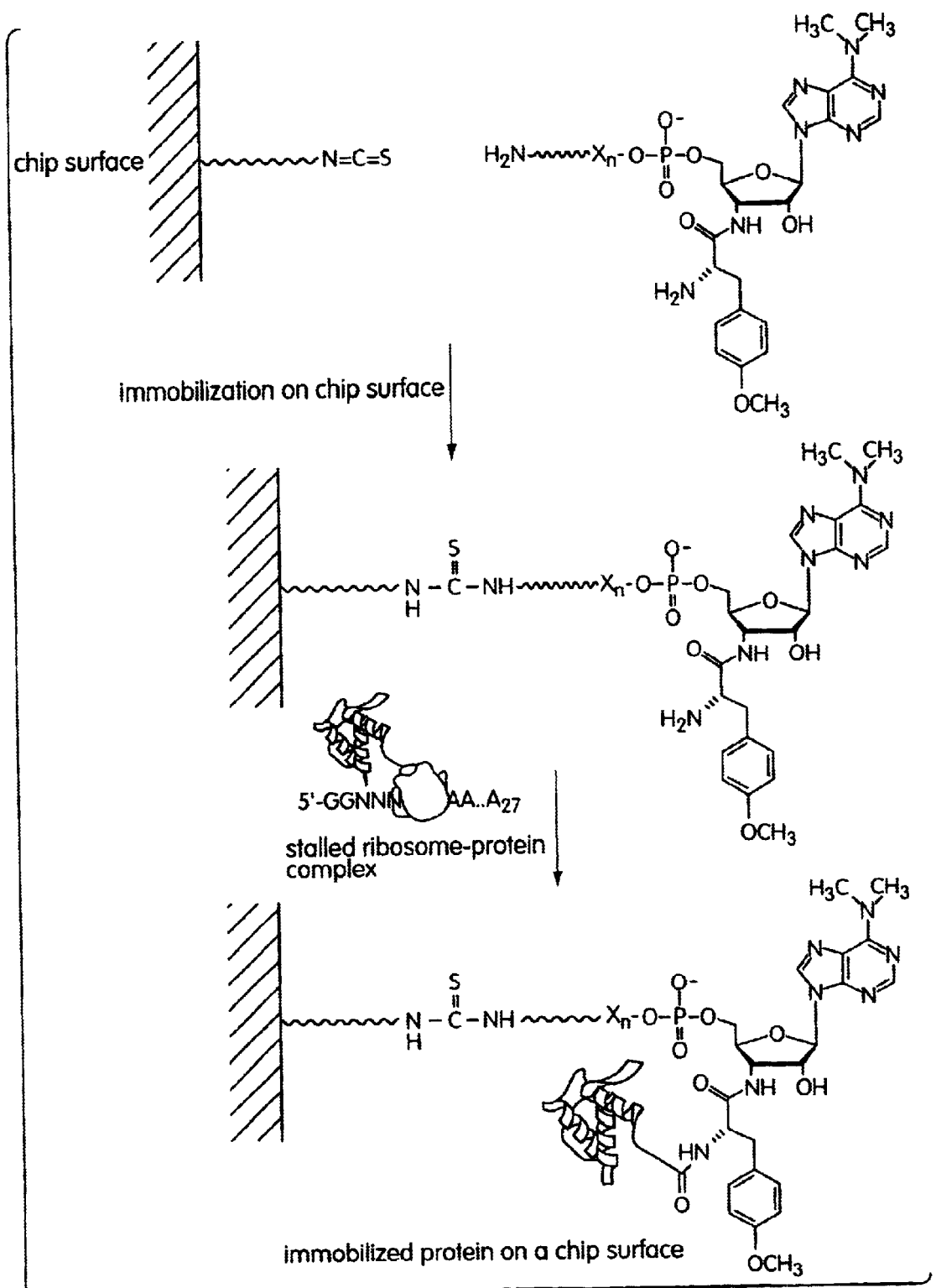
FIG. 9 is a schematic illustration of an exemplary method for the attachment of a 5'-terminal amino $X_n$-puromycin to an isothiocyanate-functionalized chip surface, for example, for the purpose of directed protein immobilization.

A puromycin or $X_n$-puromycin derivative with the appropriate terminal reactivity may also be used to derivatize a functionalized chip surface. The resulting "puromycin chip" may then be utilized for the direct attachment of peptides or proteins on the chip surface upon contact with stalled ribosome complexes, as illustrated in FIG. 9. In this example, a 5'-amino terminated $X_n$-puromycin derivative is used to functionalize a chip surface premodified with isothiocyanate groups (as described, for example, in Kuimelis et al., U.S. Ser. No. 09/282,734, entitled Addressable Protein Arrays, filed Mar. 31, 1999; and Kuimelis et al., WO 99/51773). The tethered puromycin then directs the attachment of proteins through their C-terminus upon reaction with stalled ribosome complexes.

In yet another embodiment, puromycin may be linked to polymers. In one particular example, puromycin may be attached to an oligonucleotide using previously described methods (Szostak et al., WO 98/31700; Szostak et al., U.S. Ser. No. 09/247,190 (1999), now U.S. Pat. No. 6,261,804 B1; Roberts & Szostak (1997) Proc. Natl. Acad. Sci. USA 94:12297–12302) for the purpose of sequence-specific hybridization to a solid phase.

Figure 10:
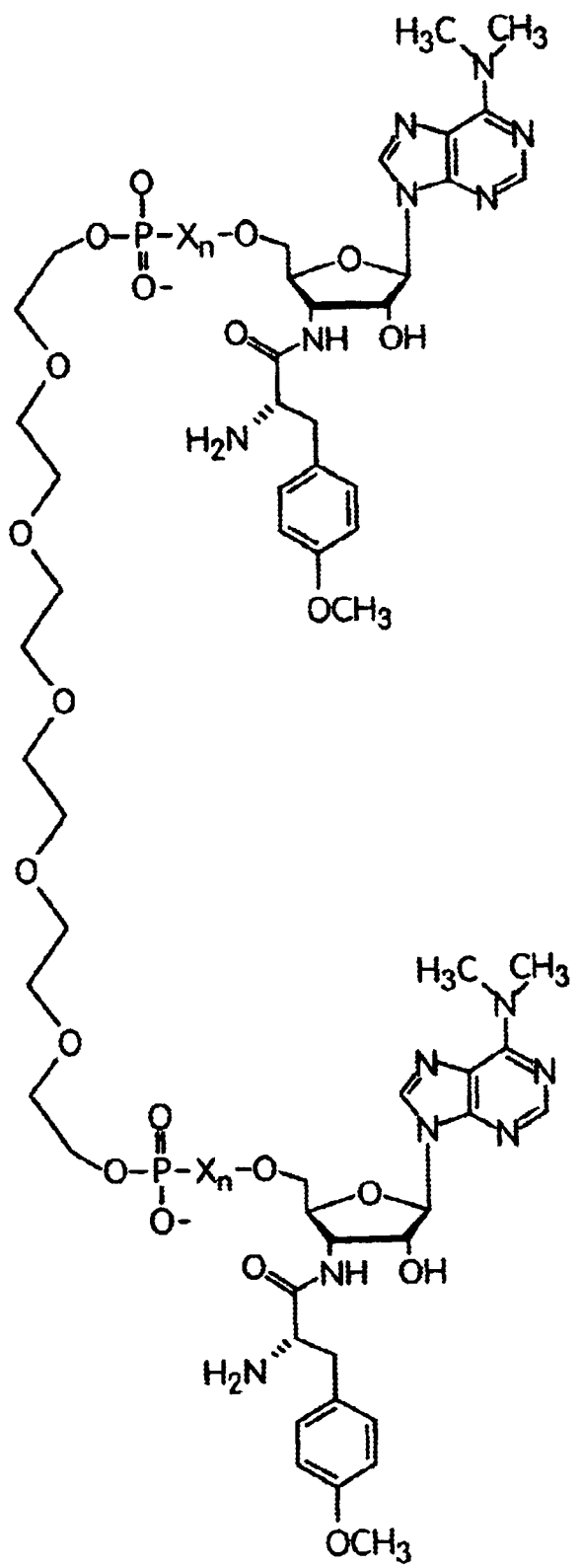
FIG. 10 is a schematic illustration of an $X_n$-puromycin 5'-phosphate dimer linked through a polyethylene oxide chain.

An appropriate puromycin- or $X_n$-puromycin-tag may also be used for the preparation of protein-protein conjugates. In one example, a puromycin or $X_n$-puromycin dimer (FIG. 10) may be added to stalled ribosome complexes to generate protein homodimers. Puromycin or $X_n$-puromycin dimers are prepared as described above for FIG. 2 using a second puromycin or puromycin derivative as a tag.

Figure 11:
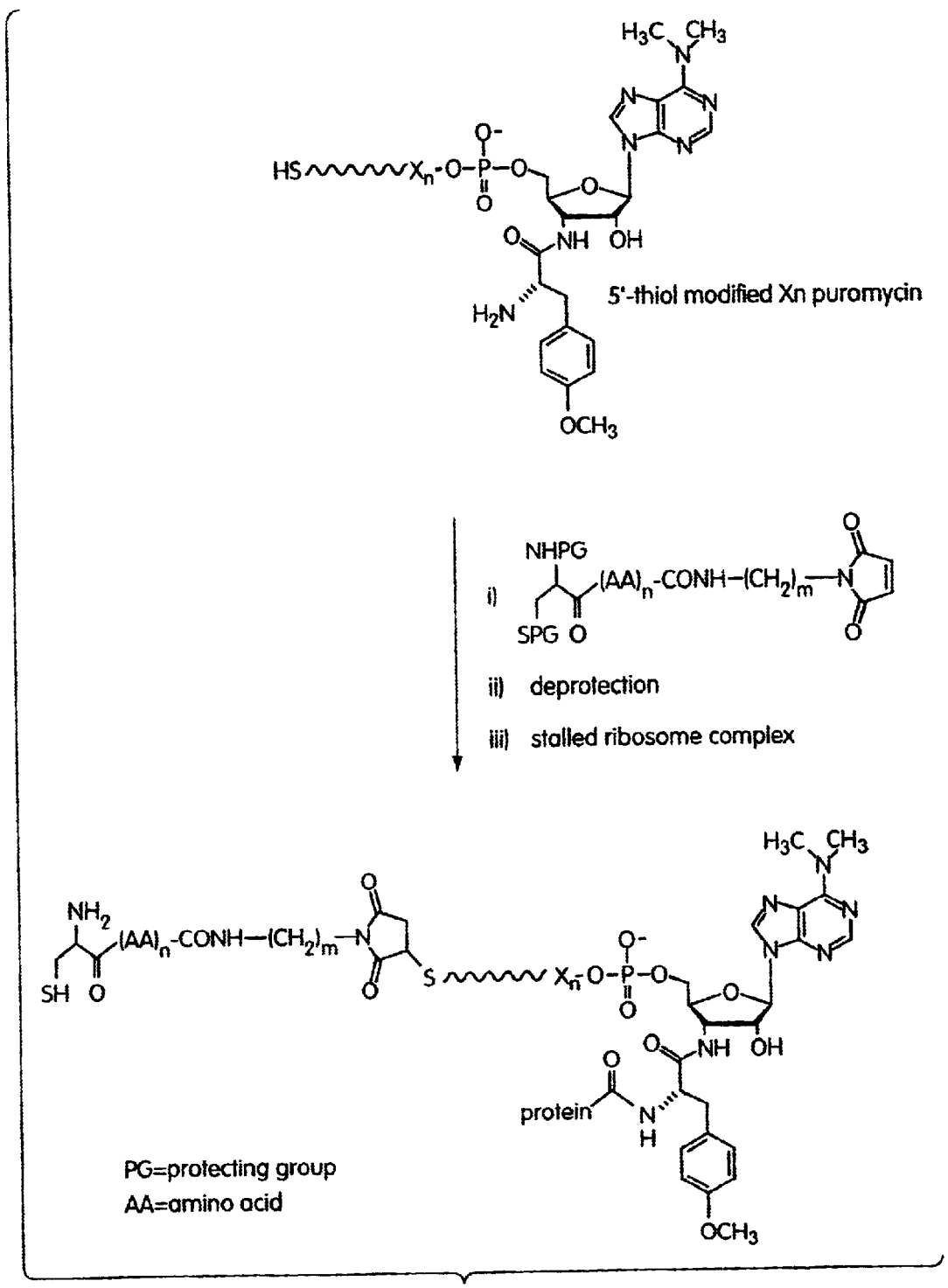
FIG. 11 is a schematic illustration of an exemplary method for the production of a 1,2-aminothiol puromycin derivative.

In an alternative synthetic scheme, protein-polymer conjugates may be prepared using a step-wise approach. In the first step, a puromycin or $X_n$-puromycin derivative carrying a 5'-cysteinol moiety is used to introduce a 1,2-aminothiol reactive group into a protein. An example of the preparation of this modified protein is outlined in FIG. 11. In this example, a puromycin or $X_n$-puromycin derivative carrying a 5'-terminal thiol moiety is alkylated with a suitable protected N-terminal cysteinyl peptide carrying a thiol-reactive maleimide group at its C-terminus (as described, for example, in Boeckler et al. (1998) Bioorg. Med. Chem. Lett. 8:2055–2058). In the second step, polymers (for example, proteins, nucleic acids, or unnatural polymers) or a solid phase (for example, a column, plate, tube, bead, or chip) carrying a thiolester group are linked to the 1,2-aminothiol-tagged protein under physiological conditions using an orthogonal ligation strategy, as described, for example, in Methods for the Preparation of Nucleic Acid-Protein Conjugates, Dawson et al. (1994) Science 266: 776; Ni et al. (1998) J. Am. Chem. Soc. 120: 1645; and McPherson et al. (1999) Syn. Lett. S1: 978–980.

Figure 12:
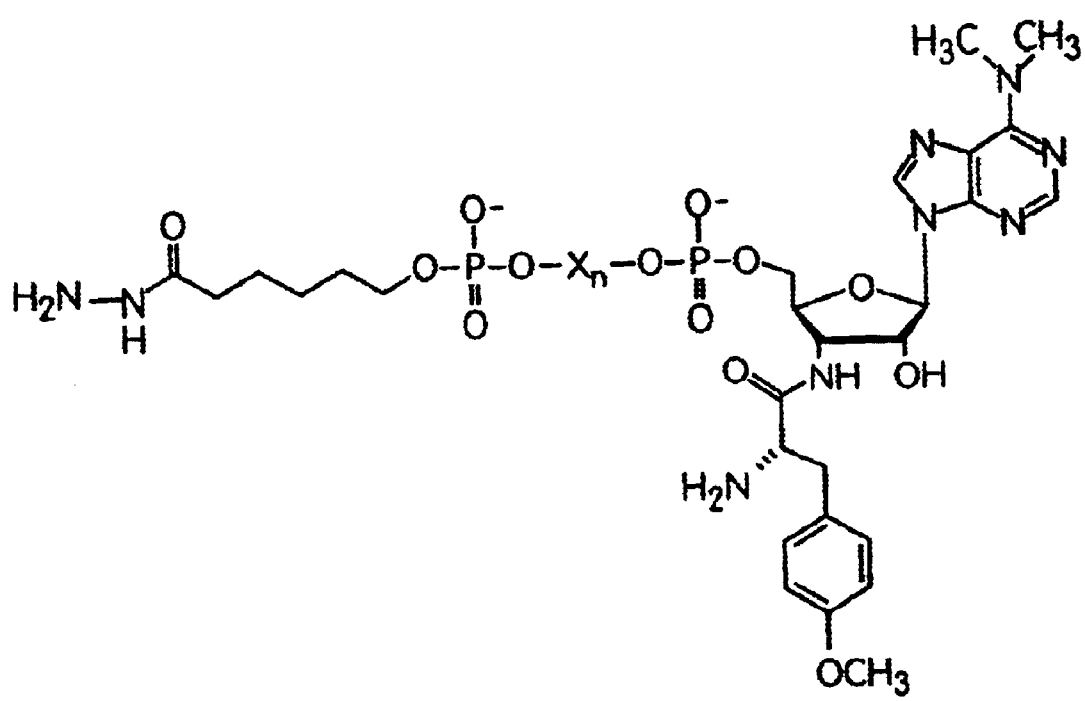
FIG. 12 is a schematic illustration of an $X_n$-puromycin-5'-phosphate carrying a 5'-terminal hydrazide group.

Alternatively, a puromycin or $X_n$-puromycin derivative carrying a 5'-terminal hydrazide group, as shown in FIG. 12, may be used to introduce a C-terminal hydrazide nucleophile into the protein (Lohse et al., DNA-Protein Fusions and Uses Thereof, U.S. Ser. Nos. 60/110,549; 09/453,190 (1999); and WO 00/32823). Reaction of the hydrazide with a cabohydrate aldehyde or ketone group under physiological conditions may be used to generate protein-carbohydrate conjugates (as described, for example, in Gahmberg & Tolvanen (1994) Meth. Enzymol 230: 32–44).

To maximize the yield of the C-terminally tagged product, the tag is preferably attached to the full-length peptide or protein following translation of the open reading frame. This can be achieved by stalling the ribosome as an mRNA-ribosome-peptidyl complex after translation of the coding sequence. Ribosome stalling at the 3'-end of the open reading frame may be accomplished by any of a number of different methods. In one preferred approach, the message is engineered to be devoid of stop codons. As a result, release factors cannot bind, and the ribosome stalls (see, for example, Hanes & Plueckthun (1997) Proc. Natl. Acad. Sci. USA 94: 4937–4942). In another preferred approach, a DNA oligomer may be linked to the end of the message causing the ribosome to pause; this technique is described in Szostak et al., WO 98/31700; Szostak et al., U.S. Ser. No. 09/247,190 (1999), now U.S. Pat. No. 6,261,804 B1; and Roberts & Szostak (1997) Proc. Natl. Acad. Sci. USA 94: 12297–12302). Alternatively, an in vitro translation lysate may be utilized which is devoid of release factors, as described in Lipovsek et al., Methods for Optimizing Cellular RNA-Protein Fusion Formation, U.S. Ser. No. 60/096, 818; U.S. Ser. No. 09/374,962 (1999), now U.S. Pat. No. 6,312,927; and WO 00/09737.

The yield of the reaction of tagged puromycin with stalled ribosomes depends on the Kd of the puromycin derivative for the peptidyl transferase site, the concentration of tagged puromycin, and reaction conditions like buffer, temperature, and time. For example, in a preferred approach, the synthetically prepared puromycin derivative may be incubated under conditions known to stabilize stalled ribosomes (see, for example, Hanes & Plueckthun (1997) Proc. Natl. Acad. Sci. USA 94: 4937–4942). The concentration of tagged puromycin supplied to the stalled ribosomes should preferably be above the Kd of tagged puromycin for the ribosomal peptidyl transferase. Concentrations of 5'-tagged puromycin derivatives in the low mM range (or even the low $\mu$M range) allow efficient incorporation of the tag, considering the Kd of unmodifed puromycin is in the micromolar range (see, for example, Pestka (1974) Meth. Enzymol. 30: 479–488; Vince et al. (1986) J. Med. Chem. 29: 2400–2403).

Following ribosome-catalyzed peptidyl transfer onto bound puromycin, the tagged protein may be released by addition of washing buffer containing EDTA (see, for example, Hanes & Plueckthun (1997) Proc. Natl. Acad. Sci. USA, vol. 94, pp. 4937–4942). If desired, the tagged protein may then be purified using any appropriate biochemical purification protocol. In a preferred technique, the tag itself may be used to isolate the protein, for example, by affinity chromatography. Simple washing procedures may also be utilized if the puromycin is tethered to a solid phase; in this approach, the tagged protein is retained on the solid support and impurities removed in the wash solution.

Experimental Results

The myc epitope was chosen as an example to highlight the general tagging strategy described above. Myc dsDNA was generated by standard methods of PCR to include a 5'-T7 promoter for in vitro synthesis of mRNA using T7 polymerase and a deletion mutant of the tobacco mosaic virus 5'-UTR to induce efficient translation initiation in rabbit reticulocyte lysates. The 3'-end of the myc construct was devoid of stop codons to prevent protein release from the ribosome.

Transcription of the myc PCR product (using the MegaSHORTscript kit, Ambion) gave large quantities of RNA using T7 RNA polymerase. Purified RNA was then subjected to a splinted ligation reaction with a 5'-phosphorylated $dA_{30}$ oligonucleotide catalyzed by T4 DNA ligase. The 3'-$dA_{30}$ region facilitates ribosomal stalling and thereby increases the proportion of RNA-ribosome-protein complexes available for labeling. The purified myc-$dA_{30}$ construct was then translated in rabbit reticulocyte lysate (Ambion) with $^{35}$S-methionine and stalled under high salt conditions (500 mM KCl, 20 mM $MgCl_2$).

Biotin-TEG-dCdC-puromycin (130 $\mu$M) was then added to the stalled translation reaction and labeling was allowed to take place. Biotin-TEG-dCdCdA was used as a control. The radiolabled myc peptide was then isolated by immunoprecipitation with an anti-myc monoclonal antibody (Chemicon) and protein A sepharose (Sigma). Control and C-terminally-labeled peptide were then applied to a microscope slide prefunctionalized with NeutrAvidin™ (Pierce). Visualization by phosphorimaging revealed the biotin-dependent immobilization of myc epitope to the chip surface; no significant label was associated with the negative control.

In a separate set of experiments, similar tagging of the fibronectin type III domain was also carried out to demonstrate the utility of the present tagging strategy for the immobilization of proteins with well-defined structural folds. Fibronectin is a large multi-domain protein that plays a fundamental role in cell-cell interactions and extracellular matrix formation. The repeating domains display immunoglobulin-like features that are widely involved in mammalian molecular recognition. A DNA construct of the tenth repeat of the human fibronectin type III domain (8 kDa, 10Fn3) was created that included a region encoding an N-terminal $His_6$ tag in addition to 5'-T7 promoter and TMV UTR regions.

Transcription (MegaSCRIPT, Ambion) of the $^{10}$Fn3 PCR product gave large amounts of RNA for subsequent enzymatic ligation to a $dA_{30}$ oligonucleotide. Translation in rabbit reticulocyte lysate, stalling, and labeling with biotin-TEG-dCdC-puromycin were performed as outlined in the myc experiment. $^{10}$Fn3 protein was isolated from excess biotinylated puromycin analogue by affinity chromatography on a $Co^{2+}$-NTA column (Talon™, Clontech). Application of $^{10}$Fn3 to a chip surface prespotted with NeutrAvidin™ protein and phosphorimaging analysis revealed the presence of radiolabeled $^{10}$Fn3.

The above experiments demonstrated that puromycin-mediated in vitro attachment of labels to the C-termini of peptides or proteins is a powerful technique for the regiospecific introduction of non-natural functionality into biomolecules. The puromycin analogues can be synthesized using standard oligonucleotide chemistry to include, for example, fluorophores, spin labels, purification handles, or a combination thereof. One distinct advantage of this approach is that labeling is performed under in vitro conditions that are compatible with maintaining the biological activity of the protein. Moreover, this tagging approach is amenable to a high throughput format of protein labeling for screening for biomolecules of therapeutic interest.

Other Embodiments

Other embodiments are within claims.

All publications, patents, and patent applications mentioned herein are hereby incorporated by reference.

What is claimed is:

1. A method for C-terminal protein tagging, comprising
    (a) providing a nucleic acid sequence encoding a protein;
    (b) translating said nucleic acid sequence under conditions in which translation stalls at the 3' end of said nucleic acid sequence, forming a stalled translation complex comprising said protein; and
    (c) contacting said stalled translation complex with a puromycin-tag under conditions in which said puromycin-tag is covalently bonded to the C-terminus of said protein.

2. The method of claim 1, wherein the tag of said puromycin-tag is attached to the 5'-hydroxy group of the puromycin.

3. The method of claim 1, wherein said tag is attached to the 5'-hydroxy group of said puromycin through a phosphate group.

4. The method of claim 1, wherein said nucleic acid sequence encoding said protein contains no stop codons.

5. The method of claim 1, wherein said translating step (b) is carried out in the substantial absence of at least one translation release factor.

6. The method of claim 1, wherein the 3'-end of said nucleic acid sequence encoding said protein is covalently linked to a DNA oligomer.

7. The method of claim 1, wherein the tag of said puromycin-tag is a small molecule.

8. The method of claim 7, wherein said small molecule is biotin.

9. The method of claim 1, wherein the tag of said puromycin-tag is a detectable label.

10. The method of claim 9, wherein said detectable label is fluorescein, rhodamine, or BODIPY, or a derivative thereof.

11. The method of claim 1, wherein the tag of said puromycin-tag is a functional group.

12. The method of claim 1, wherein said protein has a first functional group and the tag of said puromycin-tag is a second functional group and wherein said first functional group has a reactivity orthogonal to the reactivity of said second functional group.

13. The method of claim 1, wherein the tag of said puromycin-tag is a tether for attachment to a solid support.

14. The method of claim 13, wherein said solid support is a column, bead, or chip.

15. The method of claim 1, wherein the tag of said puromycin-tag is one member of a specific binding pair.

16. The method of claim 15, wherein said one member comprises a phenyl diboronic acid.

17. The method of claim 1, wherein a nucleotide sequence is positioned between the tag and the puromycin of said puromycin-tag.

18. The method of claim 17, wherein said nucleotide sequence is between about 1–200 nucleotides in length.

* * * * *